United States Patent [19]

Lassy

[11] 4,205,684
[45] Jun. 3, 1980

[54] REFLECTIVE DEVICE FOR SUNBATHING

[76] Inventor: Fred H. Lassy, 161 Timberline Rd., Warwick, R.I. 02886

[21] Appl. No.: 934,905

[22] Filed: Aug. 18, 1978

[51] Int. Cl.² .......................... A61N 5/00; A61N 5/06
[52] U.S. Cl. ................................................... 128/372
[58] Field of Search ............................. 128/371–374, 128/362, 395; 135/5 R; 52/71, 74, DIG. 10; 16/171, 175, 176, 150

[56] References Cited

U.S. PATENT DOCUMENTS

| 2,981,256 | 4/1961 | Besnah | 128/372 |
| 3,023,753 | 3/1962 | Wheless | 128/372 |
| 3,050,067 | 8/1962 | Trafton | 128/372 |
| 3,496,941 | 2/1970 | Ketner | 128/372 |
| 3,902,753 | 9/1975 | Wilson | 5/344 X |
| 3,991,769 | 11/1976 | Paz | 128/372 |

Primary Examiner—Robert W. Michell
Assistant Examiner—Jeffrey W. Tayon
Attorney, Agent, or Firm—Barlow & Barlow

[57] ABSTRACT

A reflective device is disclosed which forms an enclosure, the self supporting walls of the device being provided with a highly reflective surface which will reflect and spread light rays, particularly those of the ultraviolet spectrum. The enclosure is made of a plurality of panels that are hingedly and flexibly interconnected in such a way that in the preferred embodiment the device assumes the form of an inverted frustum. Panels adjust semi-automatically to a multiplicity of different angles, providing optimum reflection on a person or persons within the enclosure.

10 Claims, 16 Drawing Figures

REFLECTIVE DEVICE FOR SUNBATHING

SUMMARY OF THE INVENTION

It is generally well known that light rays are necessary to the well being and continuance of many life forms and that exposure of the human body to the ultraviolet rays of the sun can be beneficial from both a biological and an asethetic viewpoint. The object of this invention is to provide an accelerated means of obtaining skin tanning effects from the rays of the sun, especially when natural conditions are less than optimum for such endeavors, as for instance, during the fall, winter, and spring seasons of the year and also during the morning or late afternoon hours of the day when the sun is not at its' zenith in relation to the person who might be desirous of utilizing ultraviolet rays for asthetic or medicinal purposes.

The device can be used to good advantage by persons who have only a limited time for sun bathing activities and would like to get tanning effects from short exposures, without extensive travel to natural environments where this might be possible. The accelerated process of tanning the skin is accomplished in the device by supplementing and intensifying direct exposure, with the ultraviolet rays that are not only reflected, but are also spread, by the material on the surface of the panels. It is these functions of the device that make it possible to expose a human body within the enclosure and tan the skin, in temperatures that would ordinarily require heavy clothing in order to remain comfortable.

By virtue of complete portability and a simple erection process, independent of extraneous support members, the invention is well suited to usage in almost any area that affords exposure to the sun rays, such as, a terrace, patio, roof-top, poolside, or the beaches, parks, and other general resort areas. Through a simple unfolding, or folding action, the device is made ready to use, for carrying, or for storage.

The construction of the device is comprised of a plurality of panels of similar shape and size, each of said panels being formed of light-weight heat insulating sheet material of a thickness sufficient to provide a desirable self-supporting rigidity to the panel, each panel having a generally horizontally extending bottom edge construction for engaging a horizontal support surface. A pair of side edges extending upwardly from opposite ends of said bottom edge construction, and a top edge construction between the upper ends of said side edges having a horizontal extent equal to, or greater than said bottom edge construction. Means are provided for connecting said panels in side edge to side edge relation for articulated movement between (1) a collapsed storage position in which the panels are disposed in stacked relation with the side edges and top and bottom edge constructions thereof generally aligned and (2) an operative position. In the operative position the bottom edge of said panels is disposed in supported relation on a horizontal surface in a generally annularly extending relationship defining a substantially enclosed annular horizontal surface area of a size sufficient to permit an individual or individuals to recline in supported relation thereof. The panels extend upwardly and outwardly with respect to said horizontal surface area with the side edges of adjacent panels disposed in adjacent relation. In this way panels present a plurality of generally flat surfaces which are angularly related to one another and disposed at a generally similar upwardly and outwardly inclined angle with respect to said horizontal surface area. The flat surfaces of the panels have means for reflecting the sun's rays so that an individual reclining in supported relation above said horizontal surface area with said panels disposed in operative position will receive both direct and reflected concentration of the sun rays, said reflecting means being relatively thin with respect to the thickness of said panels so that the heat insulating properties of said panels as aforesaid prevent the reflecting means from retaining heat from the sun sufficient to render the same unpleasant to the touch.

DESCRIPTION OF THE PREFERRED EMBODIMENT

The device of the present invention consists of a plurality of walls or panels designated 10A thru 10J respectively, there being illustrated ten panels. Each of these panels are flexibly connected to each other and are preferably formed in a trapezoidal shape so as to define vertical side edges 11 and 12, a bottom edge 14 and a top edge 15. The arrangement is such that the bottom edge 14 is shorter than the top edge 15.

Figure 3:
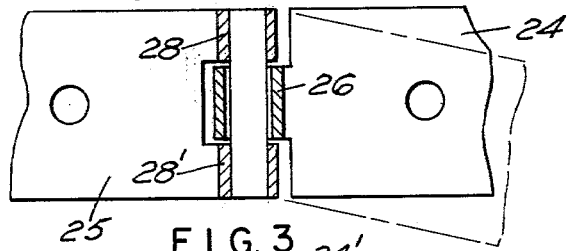
FIG. 3 is an enlarged sectional view of a typical hinge used for interconnecting the panels.
Figure 5:
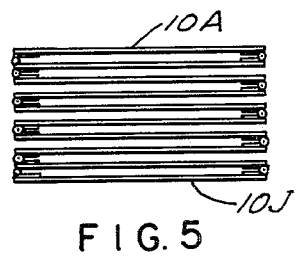
FIG. 5 is a small diagrammatic view showing the panels folded for transport.

Each wall or panel consists of a hardboard sheet cut to the proper form and suitably finished and on one surface of this hardboard aluminum foil is bonded. This forms a superior reflective construction to the utilization of Mylar which has been aluminized, since it has been found in practice that aluminized Mylar does not properly reflect the short ultraviolet wave lengths, the Mylar apparently absorbing the short wave lengths. It should be understood, however, that other types of aluminized plastic may be suitable. For example, a polyvinyl acetate does not tend to absorb the short ultraviolet wave lengths but does reflect and therefore may be substituted for the aluminum foil. The adjacent side edges of each wall are interconnected firstly by a hinge designated 20 and secondly by a flexible member or cord designated 22. It will be noted, by referring to FIG. 1, that the hinges 20 are first placed on one face of the adjacent walls or panels and then on the opposite face. This is done in order to provide an accordion folding system such as is illustrated in FIG. 5 of the drawings. The interconnecting hinges 20 are preferably specially formed, and by referring to FIG. 3, it will be seen that this, in effect, is a loose jointed hinge construction that gives up to substantially 30 degrees of free angular movement relative to the hinging axis which is shown by the broken line diagrammatically in FIG. 3. To this end, the hinge is made of two plates 24 and 25, the plate 24 having a rolled barrel 26 which will have an interior diameter of, for example, 7.94 mm. and the plate 25 will have a pair of rolled barrels 28, 28' which will have an internal diameter of approximately 4.76 mm. In this way if a press fit pin is placed within the barrels 28, the requisite 30 degree relative motion between the hinges will be attained.

The cord-like connectors 22 may be handled in a variety of fashions, but it has been found preferable to interconnect these upper sections by twisting the cord a full 360 degrees. In this way, when the panels are folded as seen in FIG. 5, it keeps the panels from touching each other so that the reflective surface will not in any way be damaged.

Figure 4:
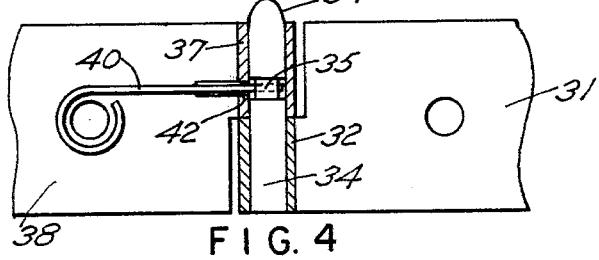
FIG. 4 is an enlarged sectional view of a slip hinge used at the entry and disconnect point for the panels.

The connecting means between walls or panels 10A and 10J are specially formed with a pair of slip joint hinges 30 which are seen in greater detail in FIG. 4 of the drawings. These particular hinges 30 are formed by making two flat plate hinges with single barrels, there being provided one hinge plate 31 with a barrel 32 into which is press fitted a pin 34 that is provided with a circular cutout portion or detent 35. The pin 34 is received in a barrel 37 of the mating hinge plate 38 and mounted on the plate 38 is a spring 40 which passes through an aperture 42 in the barrel 37 to engage the recess 35 of the pin 34, while both hinges 30 and 30' may be made in this fashion, normally the lower hinge 30' omits the spring locking means as being an unnecessary feature and merely uses a long loose pin 34' as seen in FIG. 1.

Figure 1:
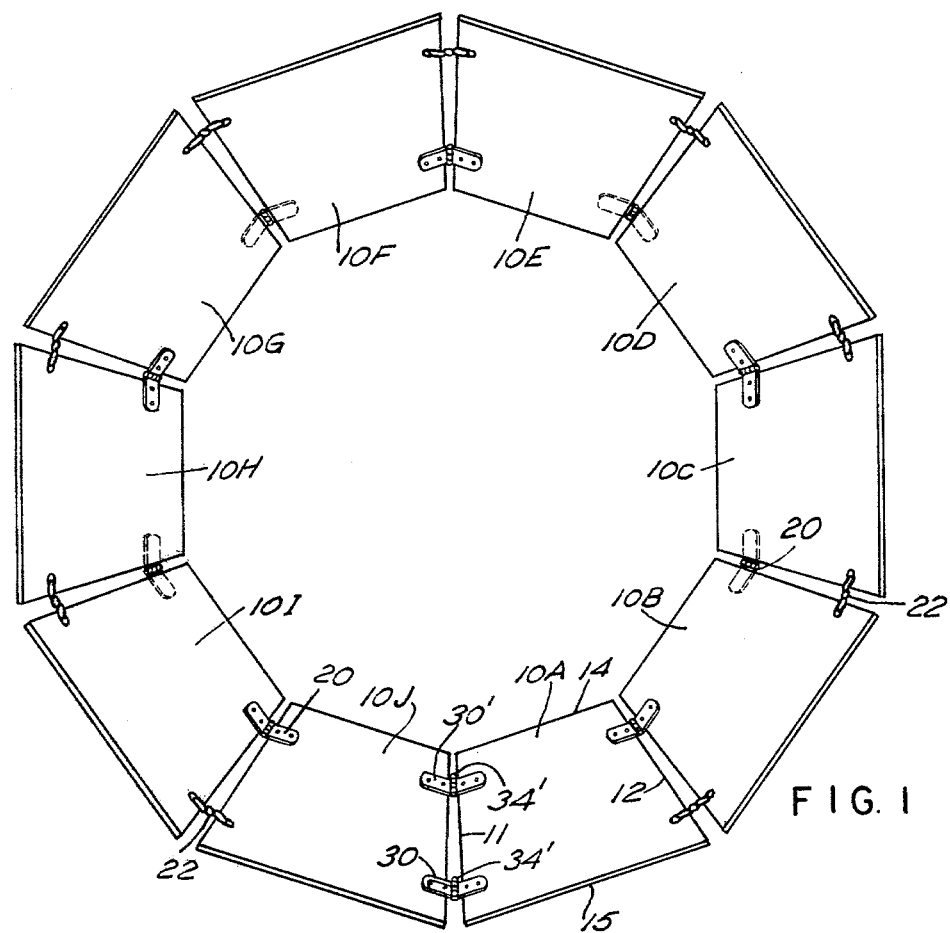
FIG. 1 is a top view of an assembled reflecting device made in accordance with the invention.
Figure 2:
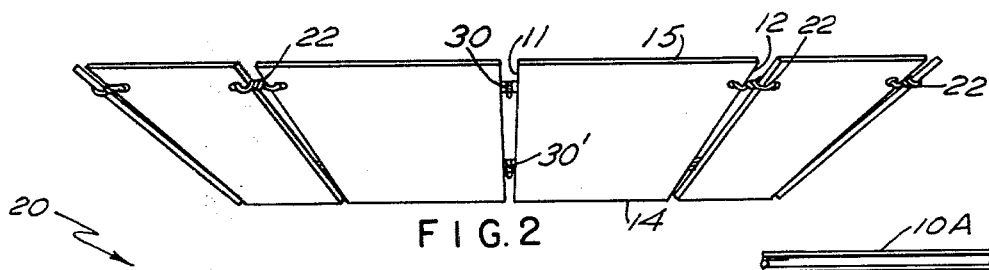
FIG. 2 is a side elevational view of the device looking from the bottom of FIG. 1 upwardly.

When the device is arranged in the manner illustrated in FIG. 1, it will be apparent that it forms effectively an inverted frustum, and because of the flexible interconnection of each of the walls or panels, the device may be readily adjusted.

Figure 7:
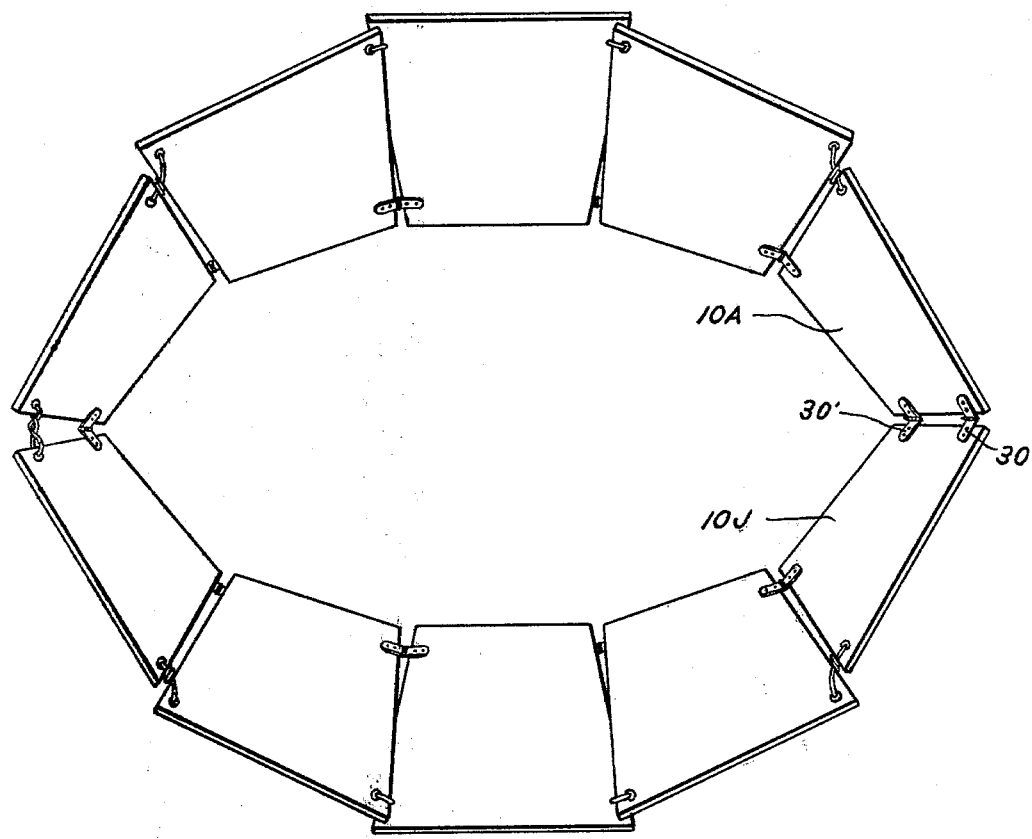
FIG. 7 is a top view showing the device in an adjusted position.
Figure 8:
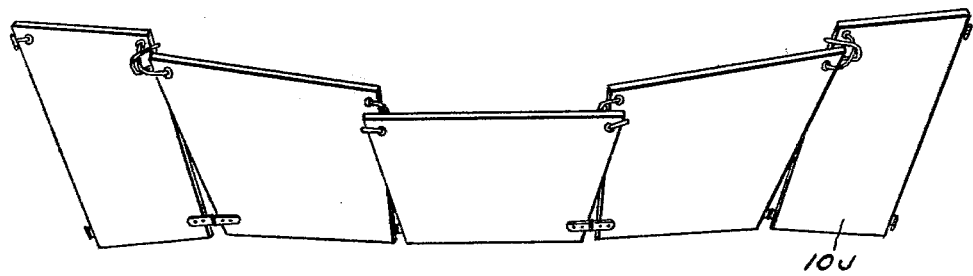
FIG. 8 is a side view of FIG. 7.
Figure 9:
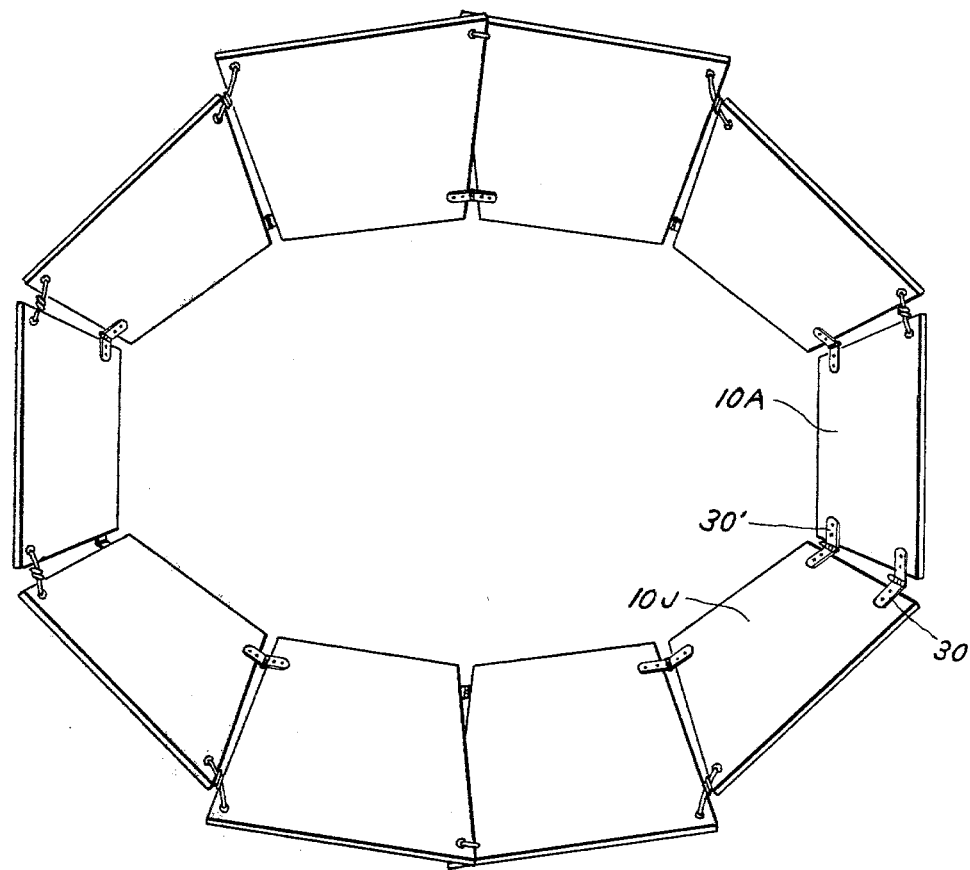
FIG. 9 is a top view showing the device in another adjusted position.
Figure 10:
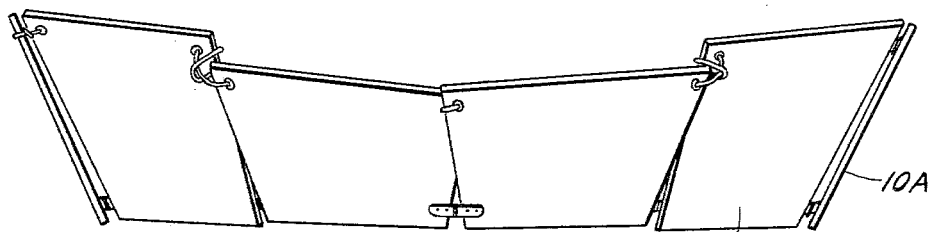
FIG. 10 is a side view of FIG. 9.
Figure 14:
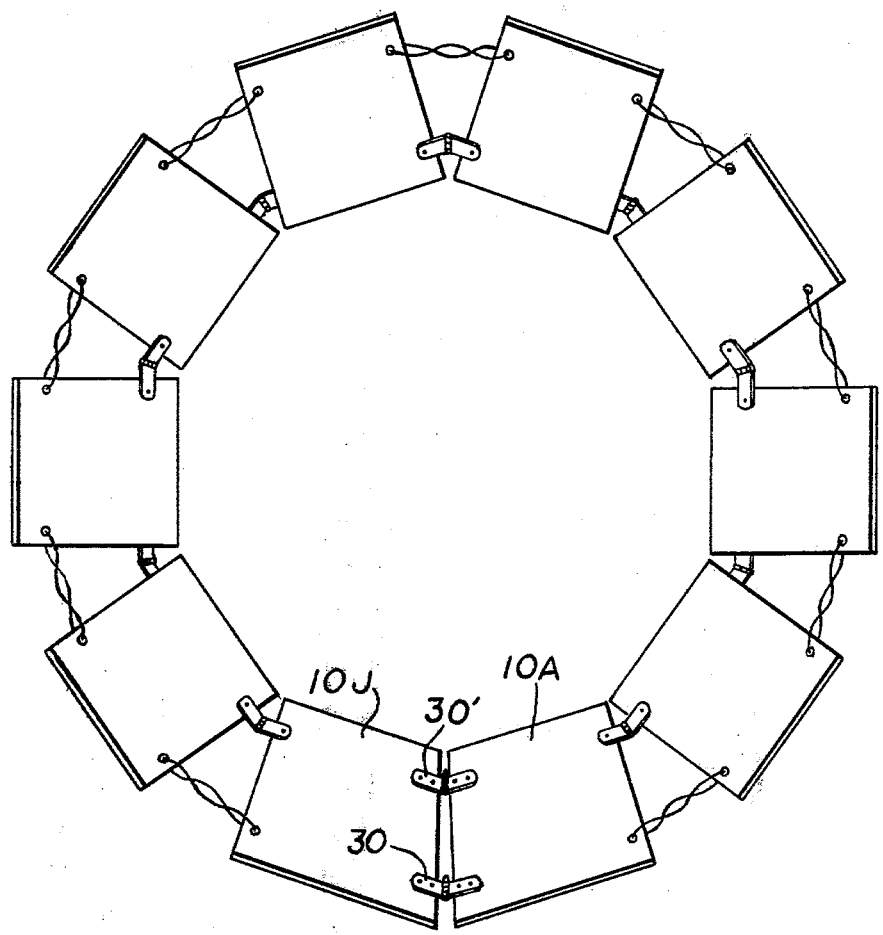
FIG. 14 is a top view of the device, utilizing rectangular panels, in an adjusted position as per FIG. 1.

One of the unique features of the instant invention is its ability to be adjusted to accommodate various declinations and transit positions of the sun and further to permit the sun to be reflected towards the body of the person who is within the enclosure at a plurality of angles. The versatility of the device can be seen by referring to FIGS. 7 thru 10 where in FIG. 7 there is illustrated the device in one possible position and particularly when looking at FIG. 8 it will be readily appreciated that the panels indeed assume any number of angles to the horizontal which in turn as related to an astronomical body, such as the sun, will mean that the angle of reflection for any given instant will vary. Similarly as seen in FIGS. 9 and 10 of the drawings a different position has been illustrated and here again the variety of angles that each panel can assume has been well shown. It will be appreciated, of course, that the multitudinous of positions that the panels assume is enhanced by the fact that they are interconnected near their bottom edges by hinge means so that the hinge structures will effectively be in tension, or compression while at the same time the upper edges of the panels are interconnected by a flexible means so that they can assume a variety of positions.

Figure 6:
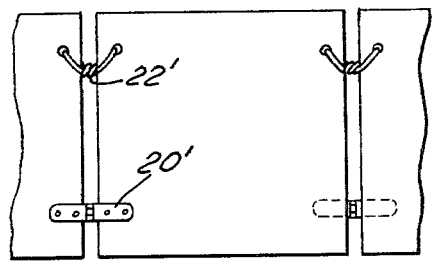
FIG. 6 is a partial elevation of a rectangular panel unit.
Figure 11:
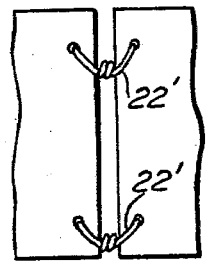
FIGS. 11 and 12 are partial elevational views of alternate forms of interconnecting the panels with cord like and plastic hinge type interconnecting means.

Also when the device is not in use, it may be readily folded by disconnecting the hinges 30 and 30' and the device folded in zigzag fashion with the aluminum foil on the inside of the exposed walls, in the position as seen in FIG. 5. In some cases, it is possible to construct the panels with complete flexible connecting means 22' as seen in FIG. 11 and to vary the configuration or outline of the panels as seen rectangular in FIG. 6. It will of course be apparent that if the flexible interconnecting means are used throughout, that when a compressive force is developed that the lower corners of the panels can overlie each other. Tension, however, is evident at the top interconnecting means in all forms in a full frustum position and is modified as the shape changes (see FIGS. 7–10).

Figure 12:
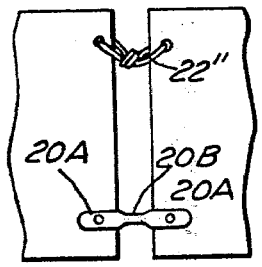
Figure 13:
FIG. 13 is a perspective view of a plastic hinge used in the FIG. 12 embodiment.
Figure 15:
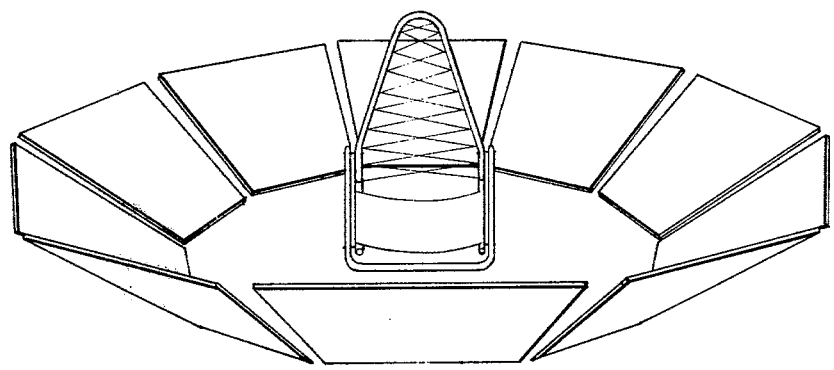
FIG. 15 is a view of the device, adjusted as per FIG. 1, with a chair shown in the enclosure.
Figure 16:
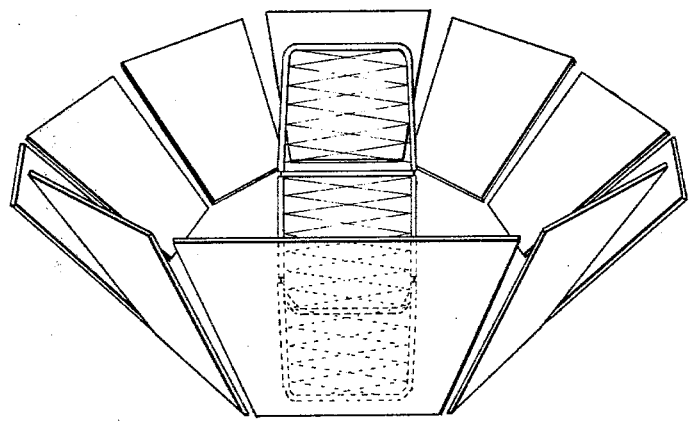
FIG. 16 is a view of the device, adjusted as per FIG. 9, with a lounge shown in the enclosure.

The interconnecting hinge may also take the form as seen in FIG. 13 where it consists of panel attaching ends 20A (illustrated as a fork) with reduced central area 20B to allow for bending flexibility, yet retain compressive stability. The completed device will be as shown in FIG. 12 with a complete flexible interconnect 22" near the upper edge of the panel.

I claim:

1. A device for reflecting light rays comprising a plurality of walls, each having a flat reflective surface and a configuration including at least a base edge, the majority of said walls being flexibly interconnected by a hinge fastener located adjacent the base edge and a flexible member spaced therefrom to assume the shape of an inverted frustum, said hinge allowing substantial angular movement whereby the wall surfaces assume different angles of repose as they are moved closer to or further from the center of the frustum.

2. A device as in claim 1 wherein each wall defines a base edge extending between two side edges to form a quadrilateral shape.

3. A device as in claim 1 wherein the walls are trapezoidal shape with the shortest side forming the base edge.

4. A device as in claim 1 wherein the hinge fastener comprises a hinge that has a major pivotal axis that allows freedom of movement perpendicular to the axis.

5. A device as in claim 1 wherein the flexible interconnecting means at the junction of one pair of adjacent walls comprises slip joint hinges.

6. A device as in claim 1 wherein said walls comprise an even number.

7. A device as in claim 1 wherein each of said walls comprise aluminum foil bonded to relatively stiff board.

8. A device as in claim 4 or 5 wherein the interconnecting means provides a space between adjacent side edges of the walls.

9. A device as in claim 4 wherein said hinge fastener has plates that are placed on one face of adjacent walls and on the opposite face at the next wall junction whereby an accordion folding system is provided.

10. A device for reflecting and directing light rays for aesthetic and medical purposes comprising a plurality of flat, reflective, trapezoidal shaped panels, flexibly interconnected to form an enclosure in the shape of an inverted frustum, means connecting the majority of lower portion of said panels by a fastener means, said fastener means allowing substantial angular movement of said panels but resistant to compression or spreading of panel spacing at this point, means connecting the upper portion of the majority of said panels, said means being flexible couplings that allow movement of the panels in all planes and change of panel spacing at the upper portion within pre-determined limits.

* * * * *